United States Patent
Thierauf et al.

(10) Patent No.: US 8,088,965 B2
(45) Date of Patent: *Jan. 3, 2012

(54) METHOD FOR ACCELERATED WOUND HEALING USING NOVEL FIBROUS WEBBINGS

(75) Inventors: Axel Thierauf, Mallersdorf-Pfaffenberg (DE); Iwer Baecker, Düsseldorf (DE); Andreas Haisch, Berlin (DE)

(73) Assignee: Bayer Innovation GmbH, Duesseldorf (DE)

( * ) Notice: Subject to any disclaimer, the term of this patent is extended or adjusted under 35 U.S.C. 154(b) by 51 days.

This patent is subject to a terminal disclaimer.

(21) Appl. No.: 12/571,661

(22) Filed: Oct. 1, 2009

(65) Prior Publication Data

US 2010/0022932 A1 Jan. 28, 2010

Related U.S. Application Data

(62) Division of application No. 11/323,069, filed on Dec. 30, 2005.

(60) Provisional application No. 60/640,896, filed on Dec. 30, 2004.

(30) Foreign Application Priority Data

Dec. 30, 2004 (DE) .................. 10 2004 063 599

(51) Int. Cl.
*A61F 13/00* (2006.01)
*A61K 9/70* (2006.01)
*A61L 15/00* (2006.01)
*A61F 13/02* (2006.01)

(52) U.S. Cl. ............. 602/44; 602/41; 602/43; 602/48; 602/54; 424/443; 424/444; 424/445; 424/448; 523/105; 523/107; 523/111; 604/307; 604/308

(58) Field of Classification Search .............. 602/41–48, 602/50, 54; 606/213–216; 424/443–449; 523/105, 107, 111; 604/307, 308
See application file for complete search history.

(56) References Cited

U.S. PATENT DOCUMENTS

| 4,181,127 A | 1/1980 | Linsky et al. |
| 4,469,863 A | 9/1984 | Ts'o et al. |

(Continued)

FOREIGN PATENT DOCUMENTS

CN  1403163 A  3/2003

(Continued)

OTHER PUBLICATIONS

Desaulniers, et al; "Optimization of an MCF7-E3 Cell Proliferation Assay and Effects of Environmental Pollutants and Industrial Chemicals"; Toxicology in Vitro; 1998; pp. 409-422.

(Continued)

*Primary Examiner* — Patricia Bianco
*Assistant Examiner* — Keri J Nelson
(74) *Attorney, Agent, or Firm* — Norris, McLaughlin & Marcus, P.A.

(57) ABSTRACT

Methods accelerate healing of a wound by applying a multilayer bandage to the wound. The multilayer bandage has a spun-bonded webbing comprising at least one partially or completely hydrolytically condensed silicon compound and a water-impervious or semi-permeable first membrane having at least one water-insoluble polymer. The webbing has a biologically degradable or biologically resorbable structure and is brought into direct contact with the wound by placing the webbing in or on the wound.

20 Claims, 8 Drawing Sheets

U.S. PATENT DOCUMENTS

| | | | |
|---|---|---|---|
| 4,657,006 | A | 4/1987 | Rawlings et al. |
| 4,730,611 | A | 3/1988 | Lamb |
| 4,730,677 | A | 3/1988 | Pearce et al. |
| 4,773,409 | A | 9/1988 | Cilento et al. |
| 5,034,506 | A | 7/1991 | Summerton et al. |
| 5,167,613 | A | 12/1992 | Karami et al. |
| 5,216,141 | A | 6/1993 | Benner |
| 5,235,033 | A | 8/1993 | Summerton et al. |
| 5,374,429 | A | 12/1994 | Kinoshita et al. |
| 5,386,023 | A | 1/1995 | Sanghvi et al. |
| 5,602,240 | A | 2/1997 | De Mesmaeker et al. |
| 5,637,684 | A | 6/1997 | Cook et al. |
| 5,644,048 | A | 7/1997 | Yau |
| 5,914,124 | A | 6/1999 | Mahoney et al. |
| 7,385,101 | B2 | 6/2008 | Chandra et al. |
| 7,619,130 | B2 | 11/2009 | Nielsen et al. |
| 2002/0111576 | A1* | 8/2002 | Greene et al. .................. 602/42 |
| 2003/0078532 | A1* | 4/2003 | Ruszczak et al. ............... 602/46 |
| 2003/0153860 | A1 | 8/2003 | Nielsen et al. |
| 2003/0176827 | A1 | 9/2003 | Chandra et al. |
| 2003/0236478 | A1 | 12/2003 | Haddock et al. |
| 2004/0133143 | A1 | 7/2004 | Burton et al. |
| 2006/0161089 | A1 | 7/2006 | Thierauf et al. |

FOREIGN PATENT DOCUMENTS

| | | | |
|---|---|---|---|
| DE | 91043085 | U1 | 10/1991 |
| DE | 19609551 | C1 * | 7/1997 |
| DE | 10 2004 063 599 | | 7/2006 |
| EP | 00 47 492 | | 3/1982 |
| EP | 0569862 | A2 | 11/1993 |
| EP | 1 262 542 | | 12/2002 |
| EP | 0772463 | A1 | 12/2005 |
| EP | 1961808 | A2 | 8/2008 |
| JP | 03-146057 | | 6/1991 |
| JP | 05-168689 | | 7/1993 |
| JP | 2004-503328 | T | 2/2004 |
| WO | 9746265 | A1 | 12/1997 |
| WO | 0142428 | A1 | 6/2001 |
| WO | 02072163 | A1 | 9/2002 |
| WO | 03053484 | A1 | 7/2003 |
| WO | 2004060413 | A1 | 7/2004 |

OTHER PUBLICATIONS

Shahan, et al; "A Sensitive New Bioassay for Tumor Necrosis Factor"; Journal of Immunological Methods 175; 1994; pp. 181-187.

Egholm, et al; "Peptide Nucleic Acids (PNA). Oligonucleotide Analogs with an Achiral Peptide Backbone"; J. Am. Chem. Soc., ; 1992, 114 (5); pp. 1895-1897.

Ahmed, et al.; "A New Rapid and Simple Non-Radioactive Assay to Monitor and Determine the Proliferation of Lymphocytes: An Alternative to [3H]thymidine Incorporation Assay"; Journal of Immunological Methods 170; 1994; pp. 211-224.

Degreef; "How to Heal a Wound Fast"; Dermatologic Therapy vol. 16, No. 2; Apr. 1998; pp. 365-375.

Brill, et al.; "Synthesis of Oligodeoxynucleoside Phosphorodithioates via Thioamidites"; Journal of the American Chemical Society, vol. 111, No. 6; pp. 2321-2322.

Beaucage, et al.; "The Funtionalization of Oligonucleotides Via Phosphoramidite Derivatives"; Tetrahedron vol. 49, No. 10; 1993; pp. 1925-1963.

Letsinger, et al; "Phosporamidate Analogs of Oligonucleotides"; The Journal of Organic Chemistry, vol. 35, No. 11; 1970; pp. 3800-3803.

Sawai; "Synthesis and Properties of Oligoadenylic Acids Containing 2'-5' Phosphoramide Linkage"; Chemistry Letters/ The Chemical Society of Japan; 1984; pp. 805-808.

Letsinger, et al; "Cationic Oligonucleotides"; Journal of the American Chemical Society-vol. 110, No. 13; 1988; pp. 4470-4471.

Dempcy, et al.; "Synthesis of a Thymidyl Pentamer of Deoxyribonucleic Guanidine and Binding Studies with DNA Homopolynucleotides"; Proc. Nat'l. Acad. Sci. USA—vol. 92; Jun. 1995; pp. 6097-9101.

Horn, et al.; "Oligonucleotides with Alternating Anionic and Cationic Phosphoramidate Linkages: Synthesis and Hybridization of Stereo-Uniform Isomers"; Tetrahedron Letters; vol. 37, No. 6; 1996; pp. 743-746.

Mag, et al.; "Synthesis and Selective Cleavage of an Oligodeoxynucleotide Containing a Bridged Internucleotide 5'—Phosphorothioate Linkage"; Nucleis Acids Research; vol. 19, No. 7; 1991; pp. 1437-1441.

Jenkins, et al; "The Biosynthesis of Carbocyclic Nucleosides"; Chemical Society Reviews; 1995: pp. 169-176.

Egholm, et al.; "PNA Hybridizes to Complementray Oligonucleotides Obeying the Watson-Crick Hydrogen-Bonding Rules"; Nature, vol. 365; Oct. 7, 1993; pp. 566-568.

Collins, et al; "Microplate Alamar Blue Assay Versus BACTEC 460 System for High-Throughput Screening of Compounds Against Mycobacterium Tuberculosis and Mycobacterium Avium"; Antimicrobial Agents and Chemotherapy; vol. 41, No. 5; May 1997; pp. 1004-1009.

Sprinzi, et al.; "Enzymatic Incorporation of ATP and CTP Analogues in the 3' End of tRNA"; European Journal of Biochemistry; vol. 81; 1977; pp. 579-589.

Carlsson "Screening for Genetic Mutations"; Nature 365: vol. 380; Mar. 21, 1996; p. 207.

Mesmaeker, et al.; "Comparison of Rigid and Flexible Backbones in Antisense Oligonucleotides"; Biorganic & Medicinal Chemistry Letters; vol. 4, No. 3; 1994; pp. 395-398.

von Kiedrowski, et al.; "Parabolic Growth of a Self-Replicating Hexadeoxynucleotide Bearing a 3'-5' Phosphoamidate Linkage"; Agnew Chem. Int. Ed Engl.; vol. 30, No. 4; 1991; pp. 423-426.

Bello, et al.; "Recent Advances in Wound Healing"; JAMA 2000, vol. 283; Issue 6; pp. 716-718.

Hunt, et al.; "Wound Healing"; Current Surgical Way; 1991; pp. 95-108.

Findlay, et al.; "Practical Management of Pressure Ulcers"; American Family Physician; vol. 54, No. 5; 1996; pp. 1519-1528.

"Pressure Ulcer Treatment"; American Family Physician; vol. 51, No. 5; 1995; pp. 1207-1222.

Pauwels, et al.; "Biological Activity of New 2-5A Analogues"; Chemica Scripta; vol. 26; 1986; pp. 141-145.

Metzger; "Clinical and Financial Advantages of Moist Wound Management"; Home Healthcare Nurse; vol. 2, Iss. 9; 2004; pp. 586-590.

Meier, et al.; "Peptide Nucleic Acids (PNA's)—Unusual Properties of Nonionic Oligonucleotide Analogues"; Angew. Chem. Int. Ed. Engl.; vol. 31, No. 8; 1002; pp. 1008-1010.

Herdewijn, et al.; "Hexopyranosyl-Like Oligonucleotides"; ACS Symposium Series—Chap. 6; 1994; pp. 80-99.

Bolli, et al.; "α-Bicyclo-DNA: Synthesis, Characterization, and Pairing Properties of α-DNA-Analogues with Restricted Conformational Flexibility in the Sugar—Phosphate Backbone"; American Chemical Society—Chapter 7; 1994; pp. 100-117.

Knapp, M.D.; "Updates in Wound Management for the Pediatrician"; Emergency Medicine: Pediatrics Clinics of North America; vol. 46—No. 6; Dec. 1999; pp. 1201-1213.

Jung, et al; "Hybridization of Alternating Cationic/Anionic Oligonucleotides to RNA Segments"; Nucleosides & Nucleotides, vol. 13(6&7); 1994; pp. 1597-1605.

Letsinger, et al.; "Effects of Pendant Groups at Phosphorus on Binding Properties of d-ApA Analogues"; Nucleic Acids Research; vol. 14, No. 8; 1996; pp. 3487-3499.

Gao et al; "Unusual Conformation of a 3'-Thioformacetal Linkage in a DNA Duplex"; Journal of Biomolecular NMR, vol. 4; 1994; pp. 17-34.

Lelkes, et al.; "GTSF-2: A New, Versatile Cell Culture Medium for Diverse Normal and Transformed Mammalian Cells"; In Vitro Cell. Dev. Biol—Animal 33; May 1997; pp. 344-351.

Stalick; "Managing and Caring for a Patient with a Complicated Wound"; Care Study; vol. 13, No. 18; pp. 1107-1109.

Habif,; "Wound Healing"; Clinical Dermatology: A Color Guide to Diagnosis and Therapy; pp. 810-813.

Mesmaeker, et al; "Novel Backbone Replacements for Oligonucleotides"; American Chemical Society; Chapter 2; 1994; 24-39.

Lueckenote; "Nursing Care of Physiologic and Physiologic Disorders"; Gerontologic Nursing: Part Six; 1996; p. 800-808.

Pontier-Lewis; "Utilizing a Team Approach to Wound Management"; Focus on Wound Care: MEDSURG Nursing, vol. 5, No. 6; Dec. 1996; pp. 427-429.

Rebecca L. Rawls, "Optimistic About Antisense", Science/Technology; Jun. 2, 1997, No. 35, pp. 35-39.

Pressure Ulcer Treatment, "Purpose and Scope", Supplied by The British Library—"The World's Knowledge", pp. 1-26.

Garric, Xavier et al; "Growth of various cell types in the presence of lactic and glycolic acids: the adverse effect of glycolic acid released from PLAGA copolymer on keratinocyte proliferation"; J. Biomater. Sci. Polymer Edn, vol. 13, No. 11, pp. 1189-1201 (2002).

Druecke, Daniel, et al; "Modulation of scar tissue formation using different dermal regenration templates in the treatment of experimental full-thickness wounds"; Wound Repair and Regeneration, vol. 12, No. 5, pp. 518-527 (2004).

Journal of Neuroscience methods 91 "A new Alamar Blue viability assay to rapidly quantify oligodendrocyte death", Stephen A. Bach, et al., pp. 47-54; 1999.

"Gerontologic Nursing" Annette G. Lueckenotte, MS, RN CS Bosby; A Times Mirror Company, 1996.

"Synthesis of Nonionic Oligonucleotide Analogues"; Maddry, et al., Organic Chemistry Department, Southern Research Institute; Birmingham AL 35255; American Chemical Society, Chapter 3, 1994.

* cited by examiner

METHOD FOR ACCELERATED WOUND HEALING USING NOVEL FIBROUS WEBBINGS

CROSS-REFERENCE TO RELATED APPLICATIONS

This application is a division of application Ser. No. 11/323,069, filed Dec. 30, 2005, now pending and claims benefit of provisional application Ser. No. 60/640,896, filed Dec. 30, 2004 and German patent application DE 10 2004 063 599.4, filed Dec. 30, 2004, the disclosures of which are incorporated in their entirety herein by reference.

FIELD OF THE INVENTION

The present invention relates to a spun-bonded or fibrous webbing-based multilayer bandage useful for accelerated wound healing.

BACKGROUND OF THE INVENTION

A moist wound closure is known in the prior art (Blank, Wundversorgung und Verbandwechsel, Kohlhammer-Verlag, Stuttgart, 2001; Stalick, Br J Nurs 2004, 13(18):1107-1109; Metzger, Home Health Nurse 2004, 22(9):586-590). The problem with this type of wound treatment is that the contact medium, for example, bandage gauze, plaster, etc., may concrete with the wound during the heal-over process. As the contact medium is subsequently removed, the wound is frequently reopened, which results in the destruction and removal of the newly generated tissue. Clearly, the wound healing process is unnecessarily slowed down as a result. When using wound dressing pads that do not adhere to the wound, thereby preventing concretion of the dressing pad with the wound, the wound defect nevertheless lacks a support and guide structure to which the newly formed tissue is oriented and on which it can grow. This condition leads, particularly in the case of deep wounds, to the formation of a substantive defect. A further consequence is the formation of unnecessary and undesirable scarring. In clinical practice, this problem extends to all wounds that involve not only the epidermis, but the corium as well and, where applicable, the subcutis (so-called "deep" wounds), and requires reconstitution of both the epidermal layers, the corium and, where applicable, the subcutis.

The thickness of the epidermis (upper dermal layer) normally varies and, depending upon location, can measure from 0.03 to 4 mm. Age and sex influence the thickness of the epidermis as well. The epidermis contains no blood vessels, and is formed from keratinocytes. Keratinocytes are horn cells which possess a cell nucleus and which produce keratic material, or keratin. Keratin is water repellant and imparts resiliency to the skin tissue.

The underlying corium is a resilient layer of skin tissue containing a high ratio of loosely intertwining connective tissue. This layer may also vary in thickness, depending upon location. On the penis and eyelids the corium is a mere 0.3 mm in thickness, whereas on the hands and soles of the feet, it can measure as much as 2.4 mm.

The aforementioned problems concern both slow-healing or completely non-healing wounds, such as the chronic diabetic-neuropathic ulcus, ulcus cruris, decubitus wounds and secondary healing wounds, as well as non-irritating, primary healing wounds (for example, ablative lacerations, excoriations (in which tissue has been grazed and thereby removed from the wound), and split thickness removal sites.

Biologically degradable and/or resorbable fiber structures (silicon gel-fibers and fiber structures) are known from German patent application DE-C 196 09 551 (incorporated herein in its entirety by reference). These fiber structures are obtained by drawing fibers from a spun composition and optionally drying them. The spun composition contains one or more partially or completely hydrolytically condensed silicon compounds derived by hydrolytic condensation of monomers of the general formula $SiX_4$, wherein residues $X_1$, $X_2$, $X_3$, and $X_4$ are identical or different and are either hydroxyl, hydrogen, halogen, amino, alkoxy, alkyloxy, alkylcarbonyl or alkoxycarbonyl, or are derived from alkyl-residues and can be interrupted by one or more oxygen atoms, sulfur atoms or amino groups.

Methods for producing a skin tissue graft and/or cells, tissues and organs based on the aforementioned fibrous structures are also known from WO 01/42428 and EP-A 01 262 542. PCT publication WO 01/42428 (incorporated herein in its entirety by reference) describes a method for producing a skin tissue graft, in particular a skin tissue autograft, wherein skin tissue cells are placed on the surface of a culture medium and allowed to grow. This method is characterized in that a surface element, in particular an aforementioned biocompatible, biodegradable and/or bioresorbable fiber, webbing or fabric is placed on the culture medium along with the skin tissue cells. The fibers of the surface element have a diameter ranging from about 5 μm to about 20 μm. The term "about" as used herein means approximately and refers to a range of values of plus or minus 10% of a specified value. For example, the phrase "about 20 μm" includes plus or minus 10% of 20 μm, or from 18 μm to 22 μm.

EP patent application EP-A 01 262 542 (incorporated herein in its entirety by reference) describes a method for the in vitro production of cells, tissues and organs, in which the fiber matrix (see, DE-C 196 09 511) functions as a cell support substance and/or guide structure for the extra-cellular matrix formed by the cells, and makes it possible for the cells to find a spatial orientation which permits the cells to multiply and/or to achieve their genetically determined differentiation.

Realizing the limitations and shortcomings of the prior art described above and the need for a better contact medium for accelerated wound healing, the present invention describes the developing and preparing of a contact medium, in its broadest sense a dressing, gauze, plaster, capable of contacting a wound, but without having to tolerate the aforementioned disadvantages such as concretion of the contact medium and the wound, destruction of newly formed tissue, unnecessarily slow wound healing, excessive scarring, and defective (healing) growth. Thus, the present invention provides a contact medium, in particular a multilayer bandage, for which it is possible to leave the contact medium in or on a moist wound and to leave it in place even after the wound has healed over, so as to not disrupt the healing process, to provide a guide structure for the newly forming tissue, and lastly to prevent the formation of scarring.

SUMMARY OF THE INVENTION

While the present invention may be embodied in many different forms, several specific embodiments are discussed herein with the understanding that the present disclosure is to be considered only as an exemplification of the principles of the invention, and it is not intended to limit the invention to the embodiments illustrated.

The present invention offers a solution to the above described problem. One aspect this invention describes a novel use of fibers disclosed in German patent publication DE-C 196 09 551 to produce a multilayer bandage for accelerated wound healing. The fibers are processed to form a webbing which may then be combined with many conventional bandaging means, including, but not limited to, bandaging means that are applied directly onto or in a wound. Hereinafter, this combination is referred to as a multilayer bandage, even where reference is made not to a typical bandage but rather to a plaster or compress or the like.

Thus, in a preferred embodiment of the present invention, a multilayer bandage is provided which comprises (i) a webbing for placement in direct contact with a wound having a periphery, and (ii) a first membrane comprising at least one water-insoluble polymer, wherein the first membrane is water-impervious. The first membrane may further comprise an adhesive portion, wherein the adhesive portion adheres to skin tissue at the wound periphery. Alternatively the first membrane does not comprise an adhesive portion and bonds with an adhesive which is applied to the skin tissue at the wound periphery. Between the first membrane and the webbing either no bond or a loose, frangible adhesive bond exists.

In one embodiment of the present invention, the water-insoluble polymer of the first membrane is selected from the group consisting of polypropylene (PP), polyvinylchloride (PVC) and polyurethane (PU).

In one embodiment of the present invention, the first membrane is a self-adhesive hydropolymer.

In a preferred embodiment of the present invention, the webbing may also have a biologically degradable or resorbable fiber structure. In another preferred embodiment of the present invention, the webbing is a fibrous webbing.

A preferred webbing of the present invention is a spun-bonded webbing that comprises at least one partially or completely hydrolytically condensed silicon compound. This fiber structure can be obtained by drawing threads from a spun composition wherein the spun composition comprises the at least one partially or completely hydrolytically condensed silicon compound. The silicon compound comprises a monomer of the formula $SiX_4$. $SiX_4$ is a tetravalent compound comprising residues $X_1$, $X_2$, $X_3$, and $X_4$. In one embodiment, residues $X_1$, $X_2$, $X_3$, and $X_4$ are identical. In another embodiment, residues $X_1$, $X_2$, $X_3$, and $X_4$ are different. In a preferred embodiment, residues $X_1$, $X_2$, $X_3$, and $X_4$ are independently selected from the group consisting of hydroxyl, hydrogen, halogen, amino, alkoxy, alkyloxy, alkylcarbonyl and alkoxycarbonyl. In another embodiment, residues $X_1$, $X_2$, $X_3$, and $X_4$ are derived from an alkyl and can be interrupted by an oxygen atom, a sulfur atom or an amino group. In a preferred embodiment of the present invention, residues $X_1$, $X_2$, $X_3$, and $X_4$ are ethyl.

The invention further provides a multilayer bandage wherein the webbing comprises an organic compound selected from the group consisting of a nucleotide, an amino acid and polymers thereof. A preferred organic compound is a morphogenic factor selected from the group consisting of a steroid, a cytokine, an interleukin, a bone morphogenetic protein, an antibody, TNF-α, TGF-β½, IGF, PDGF, and EGF.

In another preferred embodiment of the present invention, a multilayer bandage comprises (i) a webbing for placement in direct contact with a wound having a periphery, and (ii) a first membrane comprising at least one water-insoluble polymer, wherein the first membrane is water-impervious; and (iii) a second membrane comprising at least one water-soluble polymer and wherein the second membrane is disposed between the first membrane and the webbing. In a preferred embodiment, the water-soluble polymer is carboxymethylcellulose.

In one embodiment of the present invention, a loose, frangible adhesive bond exists between the second membrane and the webbing. In another embodiment, no adhesive bond exists between the second membrane and the webbing.

In one embodiment of the present invention, a bond exists between the first membrane and the second membrane. This bond can be a loose, frangible adhesive bond or a stable, non-frangible adhesive bond. In yet another embodiment, no bond exists between the first membrane and the second membrane.

In another preferred embodiment of the present invention, a multilayer bandage comprises (i) a webbing for placement in direct contact with a wound having a periphery; (ii) a first membrane comprising at least one water-insoluble polymer, wherein the first membrane is water-impervious; and (iii) a dressing selected from the group consisting of an alginate, a collagen sponge, a polyurethane foam, a polyurethane foam pad, a hydrocolloid, a hydrogel and a hydropolymer, and wherein the dressing is disposed between the webbing and the first membrane. In one embodiment, a loose, frangible adhesive bond exists between the dressing and the webbing. In another embodiment, no adhesive bond exists between the dressing and the webbing.

In other preferred embodiments of the present invention, (i) no adhesive bond (ii) a loose, frangible adhesive bond or a (iii) stable, non-frangible adhesive bond exists between the dressing and the first membrane.

BRIEF DESCRIPTION OF THE DRAWINGS

FIG. 4 shows adhesion of cells to the surface of a fiber (SEM analysis).

DETAILED DESCRIPTION OF THE INVENTION

Figure 1:
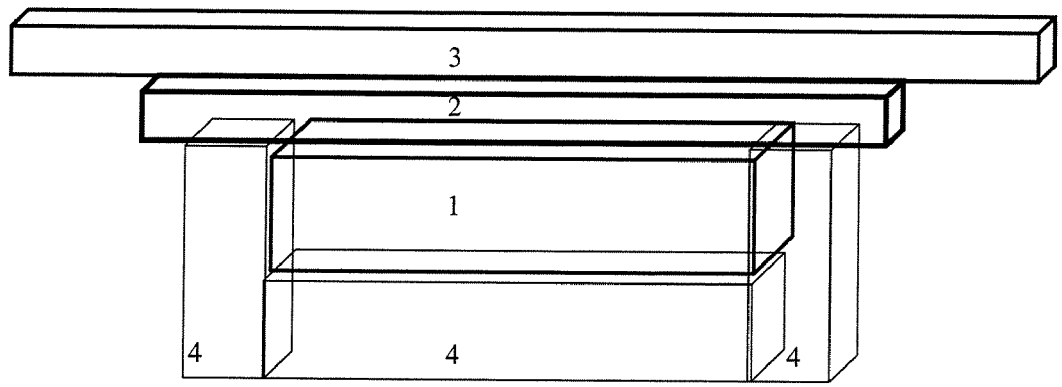
FIG. 1 shows a multilayer bandage in accordance with the present invention, fitted into a wound. 1, webbing; 2, second membrane; 3, first membrane; 4, wound.

A. Manufacturing Fibers, Webbings, Membranes and Multilayer Bandages

The present invention offers a solution to the problem described above. The present invention describes a novel use of fibers (as described in German patent publication DE-C 196 09 551) for producing and using a multilayer bandage for accelerated wound healing. The aforementioned fibers can be formed into a webbing and the webbing when brought into contact with a wound, accelerates wound healing. As used herein, "contact" or "contacting" means to place in direct physical association. The webbing may then be combined with all conventional dressings, in particular with those that are applied directly on or in a wound, i.e., brought into direct contact with the wound. This combination is referred to hereinafter as a multilayer bandage, even where reference is made not to a conventional bandage, but rather to a plaster, compress or the like. Thus, in a preferred embodiment of the present invention, a multilayer bandage comprises (i) a webbing which can be placed in direct contact with a wound having a periphery, and (ii) a first membrane comprising at least one water-insoluble polymer, wherein the first membrane is water-impervious. In one preferred embodiment, the first membrane is an adhesive plaster (adhesive bandage) as further described herein.

As previously described, moist webbings can be produced from silicon-gel fibers or fibrous structures (DE-C 196 09 551). Thus, the term "webbing" as used herein refers to a three-dimensional structure or arrangement made of fibers or fibrous structures, for example, silicon-gel fibers. The general chemical formula relating to the monomer unit is $SiO_{2-x}OH_x$ and the one relating to the polymer is $Si_n(OH)_{2x}O_{2-x}$, wherein x=0-1, that is x can be any number between 0 and 1 and including 0 and 1. For example, in one embodiment of the present invention (see further below), x is between 0.1 and 0.2 and includes 0.1 and 0.2. Webbings of the latter formula, according to the present invention, can be placed in a wound as support and guide structure and thus in direct contact with the tissue. New tissue forms at the webbing that to some extent determines the growth direction of the newly formed tissue. With respect to webbings, a differentiation is made between fibrous webbings and spun-bonded webbings. In particular, spun-bonded webbings, made of continuous single fibers, threads or single filaments, are advantageous for 3-D applications, while fibrous webbings are particularly suited to 2-D applications. The terms "single fiber," "thread" or "single filament" herein are used interchangeably.

A method for producing single fibers or single filaments is described in the German patent application DE-C 196 09 551 (incorporated in its entirety by reference). Here, one of skill in the art will recognize and appreciate that numerous parameters, such as temperature, pressure, molar ratio of individual components, chemical nature of reactants of the solvent or of catalysts may be varied to produce particularly suitable fibers and webbings, for example, webbings having high or low biodegradability and bioresorbability.

The method set forth in DE-C 196 09 551 is described once again in somewhat greater detail. In a preferred embodiment of the present invention, TEOS (tetraethoxysilane) is used as silane in a sol-gel-process. Likewise, all of the silanes or mixtures of at least two of the latter described in DE-C 196 09 551 can be used in a multilayer bandage of the present invention. Silanes useful for the methods and compositions of the present invention are commercially available or can be synthesized using methods known in the art ("Chemie und Technologie der Silicone," W. Noll, Verlag Chemie, Weinheim, 1968) and include, but are not limited to, for example, $Si(OMe)_4$, $Si(OMe)_3(OEt)$, $Si(OMe)_2(OEt)_2$, $Si(OMe)(OEt)_3$, $Si(OEt)_4$, $Si(O-i-Pr)_4$, $Si(OMe)_3(O-i-Pr)$, $Si(OMe)_2(O-i-Pr)_2$, $Si(OMe)(O-i-Pr)_3$, $Si(OEt)_3(O-i-Pr)$, $Si(OEt)_2(O-i-Pr)_2$, $Si(OEt)(O-i-Pr)_3$, $Si(O-n-Pr)_4$, $Si(OMe)_3(O-n-Pr)$, $Si(OMe)_2(O-n-Pr)_2$, $Si(OMe)(O-n-Pr)_3$, $Si(OEt)_3(O-n-Pr)$, $Si(OEt)_2(O-n-Pr)_2$, $Si(OEt)(O-n-Pr)_3$, $Si(O-i-Pr)_3(O-n-Pr)$, $Si(O-i-Pr)_2(O-n-Pr)_2$, $Si(O-i-Pr)(O-n-Pr)_3$, $Si(OMe)(OEt)_2(O-i-Pr)$, $Si(OMe)(OEt)_2(O-n-Pr)$, $Si(OMe)(OEt)(O-i-Pr)_2$, $Si(OMe)(OEt)(O-n-Pr)_2$, $Si(OMe)(O-i-Pr)_2(O-n-Pr)$, and $Si(OMe)(O-i-Pr)(O-n-Pr)_2$.

In the presence of an aqueous-alcohol solution (preferably an ethanol/water mixture according to the present invention) which serves both as a solvent (ethanol or ethanol/water) and also as a reaction partner (water) for the hydrolytic condensation, a condensation product of a suitable degree of condensation is produced at ambient temperature or at slightly reduced temperature (from about 12° C. to about 15° C.). A preferred catalyst for the condensation is an organic acid including, but not limited to, for example, citric acid, succinic acid and tartaric acid. Such acids adjust the pH of the reaction mixture to approximately 3-4. Preferably, the condensation reaction is performed at a pH below 7. Undesirable particle formation or gel-like structures have been observed at pH>7. Thus, in a preferred embodiment of the present invention, the pH of the condensation reaction is <7, preferably the pH is <6, more preferred the pH is <5, even more preferred, the pH is <4. Particularly preferred is a pH range from about 3 to about 4.

The condensation product is rendered viscous by filtration and removal of the solvent (see DE-C 196 09 551). The product can be stored for a certain time (several hours up to a few months) at temperatures below 0° C. upon formation of a so-called spinning sol (a spun composition, which is the product of the polymerization/condensation reaction). This is possible because at temperatures below 0° C. condensation occurs only very slowly.

In another preferred embodiment of the invention, a spinning sol has a solids content of approximately 10%, i.e. the solvent ratio is approximately 90%. Solids in this context refers to the condensation products, such as oligomers and oligomeric structures. Also preferred in accordance with the present invention is a time period of from about 2-3 days from the onset of the condensation reaction until the spinning sol is obtained.

In one embodiment of the present invention, a spinning sol is added to a pre-cooled (<0° C.) pressurized container, from which it is forced out under pressure through small nozzles in the form of long, non-tearing, or tear resistant threads. The threads measure approximately 10 to 100 μm in diameter and up to several meters in length (for example, 3-5 meters), depending on the size of the nozzles. As the threads are wound, their length may optionally by extended and their diameter further reduced as a result of pulling (stretching) during take up (optionally in an aqueous-alcohol atmosphere).

The threads can be wound at a speed of 100-1000 m/min, preferably at a speed of approximately 200 m/min. In one embodiment, the resultant spun threads are then passed over a roller and interlaced on a carrier strip. The threads on the carrier strip may be exposed to varying temperatures as a result of the carrier strip migrating across differing temperature zones at an operating speed of 1-10 cm/min. Thus, over the course of a condensation reaction it is possible to adjust by any desirable number the OH-groups remaining in the fibers (that is, the biodegradability and bioresorbability of the fibers). The threads can be abruptly cooled to −35° C. in the form of gel strands on the carrier strip.

In a preferred embodiment of the present invention, the interlaced threads (continuous or endless fibers) are compressed to form a spun-bonded webbing or a fibrous webbing. Compression can be performed by means of a pressure roller. In another aspect, embroidering looms (pressure rollers with needles) can be employed. The up and down motion of the needles defines a fulling process that imparts added strength to the webbing. The pressure imparted by the roller with and without needles is freely adjustable. In a preferred embodiment of the present invention, the compression force is from about 1 MPa to about 10 MPa. Next, the webbing is thermally treated, wherein temperatures vary within a range of from about −35° C. to about +65° C. Preferred is a temperature of below −5° C., more preferred a temperature of below −20° C.

Such thermal treatment yields a structurally rigid sheet simultaneously exhibiting a sufficient number of silanol-, that is, uncondensed OH-groups, in the webbing. The number of uncondensed OH-groups determines the degree of (bio)resorbability: the more uncondensed OH-groups present, the greater the (bio)resorbability. Conversely, the fewer uncondensed OH-groups, the lower the (bio)resorbability. By varying the retention times at different temperatures it is possible to adjust specifically the number of OH-groups. In a preferred embodiment of the present invention, the fibers of the webbing have approximately one OH-group per 5-10 Si-atoms, which means in the formula above for the monomer unit $SiO_{2-x}OH_x$, that x=0.1-0.2.

In a further, optional step, the webbing is thermally treated at a temperature of 50° C. or to a temperature above 50° C. in order to remove, to the extent desirable, most though not all of any remaining water and ethanol. This can be done, for example, from the solvent, as well as from the remains of the starting silane, in particular in the case of TEOS as starting silane. Thus, in a preferred embodiment of the present invention, a webbing, in particular a spun-bonded webbing, retains a sufficient amount of residual moisture. Thereby it is possible to stabilize the thermodynamically unfavorable gel state (fibers with uncondensed OH-groups in the webbing) compared to the $SiO_2$ state (fibers without uncondensed OH groups, i.e. glass fibers, in the webbing), which is more stable at room temperature. A spun-bonded webbing produced in this manner retains its gel state for a period of several months when enclosed in an airtight packaging or container. It has been found that the presence of residual ethanol, but also that of water is particularly advantageous in this regard. This may be because condensation towards $SiO_2$ ceases to continue in a (saturated) ethanol-atmosphere. This can even be reversed leading to the bioresorbability of the fibers.

The method described above is used in the production of a spun-bonded webbing. A fibrous webbing, sometimes also referred to as needle-punch webbing, may also be produced in this manner. As part of this process, the fibers are cut into pieces following the spinning step. The resultant staple fibers are 0.1-10 cm in length. Next, the staple fibers are cast onto a carrier strip, compressed, needle punched and subjected to thermal treatment of the type described above. Unlike spun-bonded webbings, fibrous webbings have no characteristic 3D-structure. Hence the latter are frequently employed in 2D applications, including, but not limited to, for example, surface wounds in the upper epidermal region. Thus, in a preferred embodiment of the present invention, a fibrous webbing is used in the treatment of a superficial wound (i.e., a wound on the surface), including, but not limited to, wounds in the upper epidermal region. In general, it can be noted that at the fiber level, fibrous webbings exhibit generally greater stabilities and are thus better suited at mechanically loaded sites, for example, preferred in treating skin tissue wounds, rather than muscle wounds.

The fiber production as described above is carried out by way of a sol-gel process on a machine that may have the following dimensions: approximately 5 m long, approximately 2 m wide and approximately 6 m high. The weight of the machine in the area below the spin tower generates a pressure ranging from about 850 to about 1,000 kg/m². Machine dimensions may, however, deviate considerably from those cited herein depending upon the equipment and productive capacity. For production, the machine requires cool water circulation with an adequate water supply and preferably a high-voltage connection.

The machine as described above is used for producing the fibers. Depending on the desired product, one or more additional processes may be added to the machine, such as a loom for producing a webbing.

Figure 3:
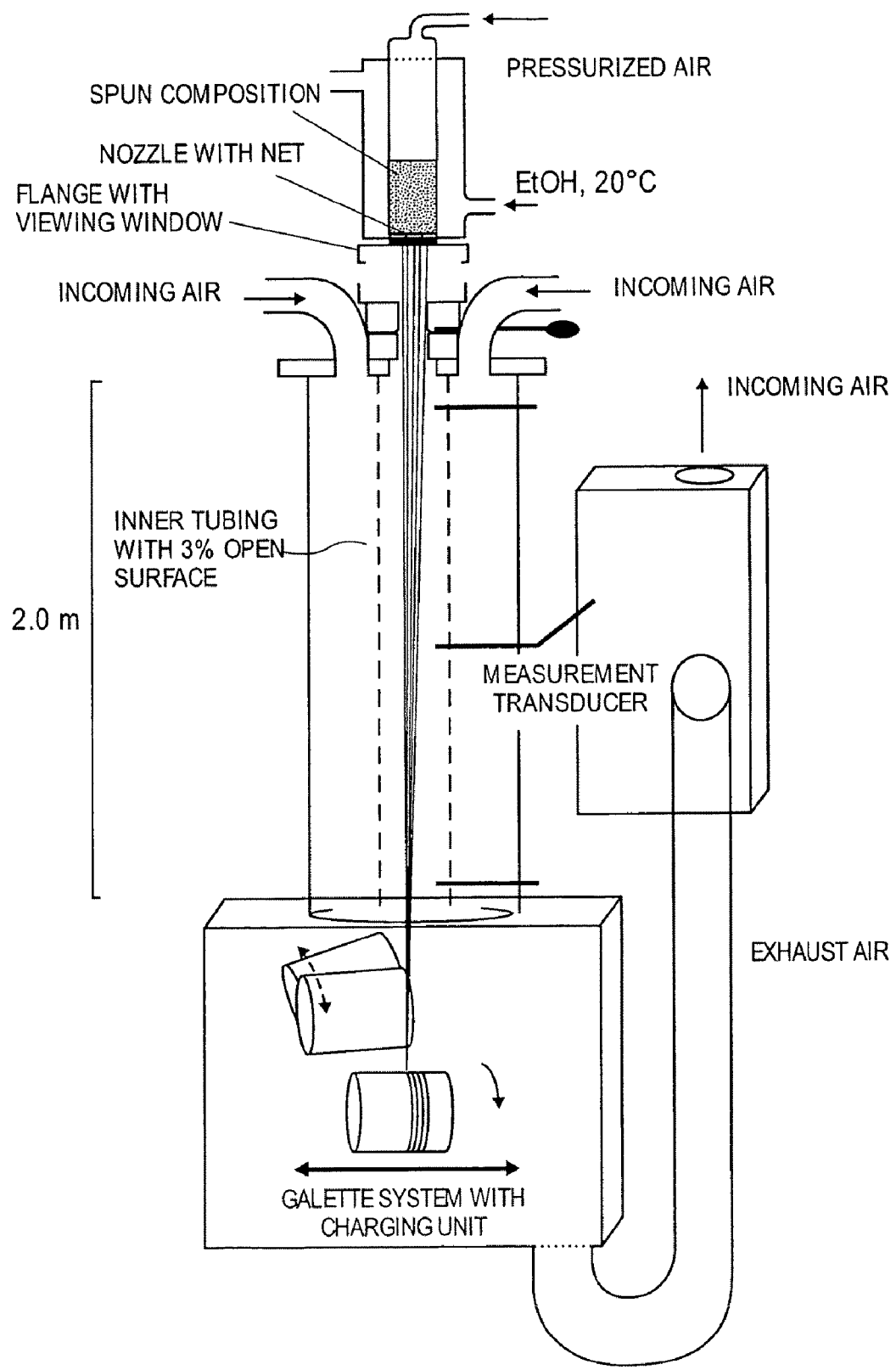
FIG. 3 shows a schematic illustration of the galette-system and the air conditioning unit.
Figure 4A:
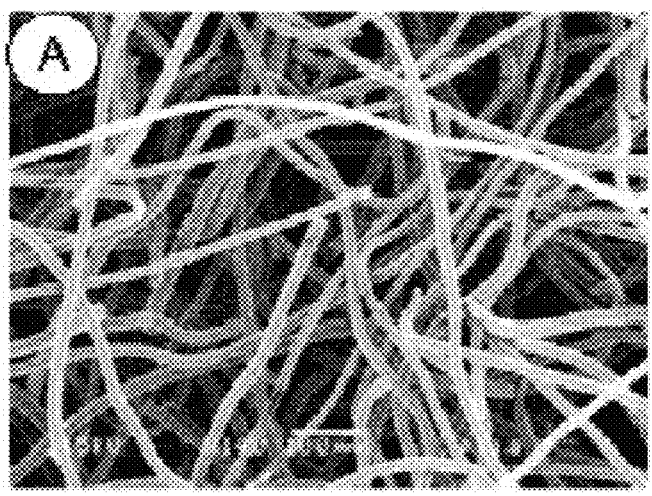
FIGS. 4A and 4B show a $SiX_4$-fiber of the present invention without cells.
Figure 4B:
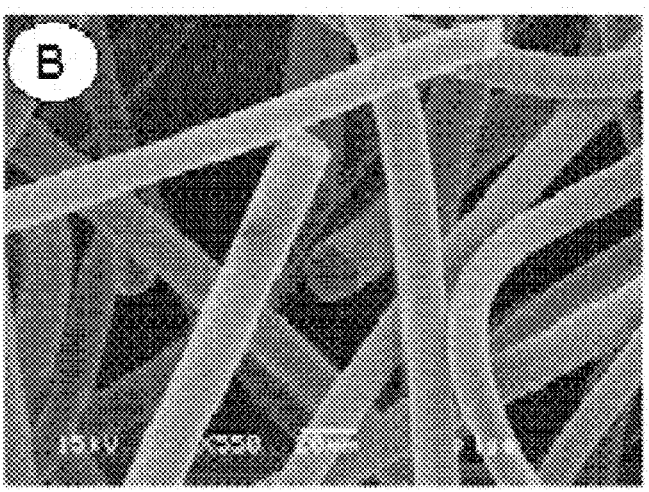
Figure 4C:
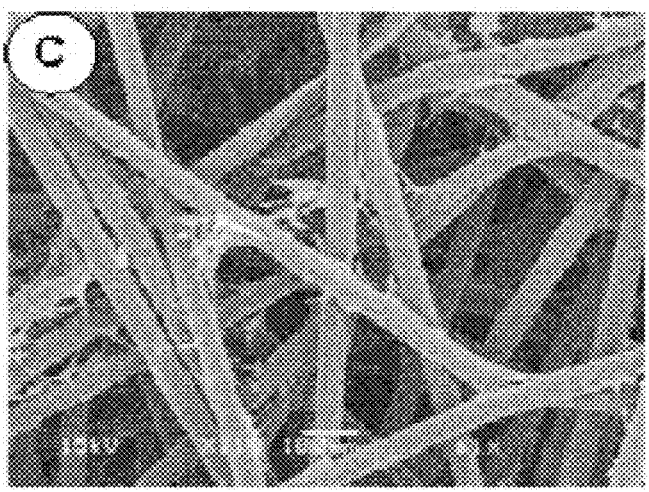
FIGS. 4C and 4D show a $SiX_4$-fiber of the present invention with cells and their excellent adhesive and spreading properties.
Figure 4D:
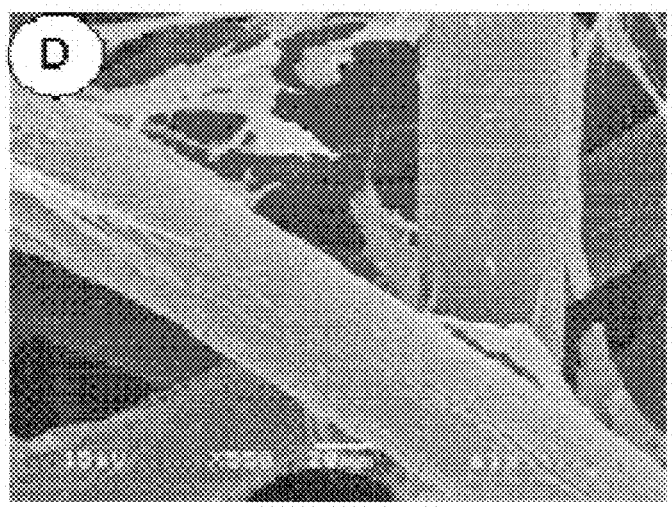
Figure 4E:
FIGS. 4E and 4F show a collagen fiber with cells, whose morphology is difficult to ascertain due to the course nature of the collagen matrix.
Figure 4F:
Figure 5A:
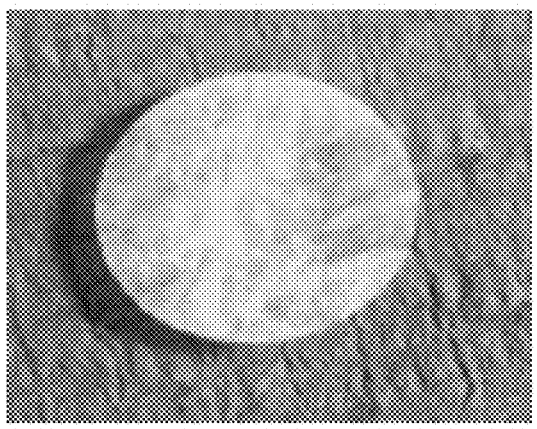
FIG. 5 shows the shape and shrink resistance of an $SiX_4$ fiber of the present invention compared with collagen fibers and PGA fibers. The left hand column, from top to bottom, shows a collagen fiber, a PGA fiber and a $SiX_4$ fiber of the present invention prior to cell cultivation. The right hand column, top to bottom, shows a collagen fiber, a PGA fiber and a $SiX_4$ fiber of the present invention four weeks after the start of cell cultivation.
Figure 5B:
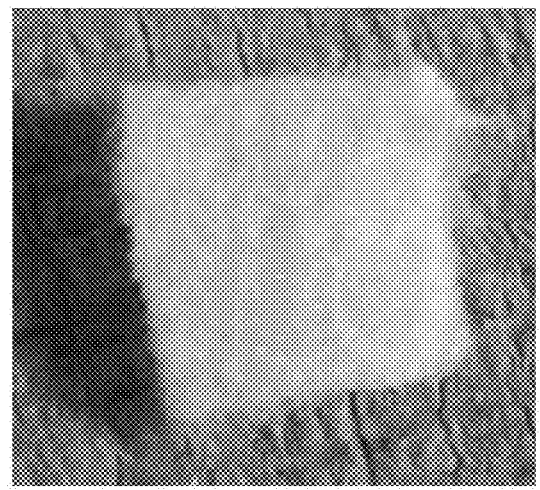
Figure 5C:
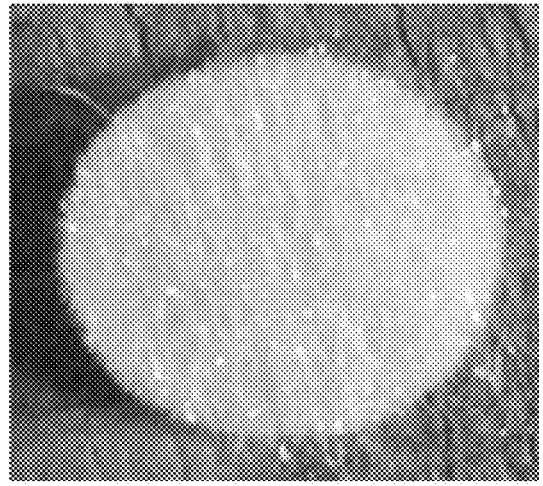
Figure 5D:
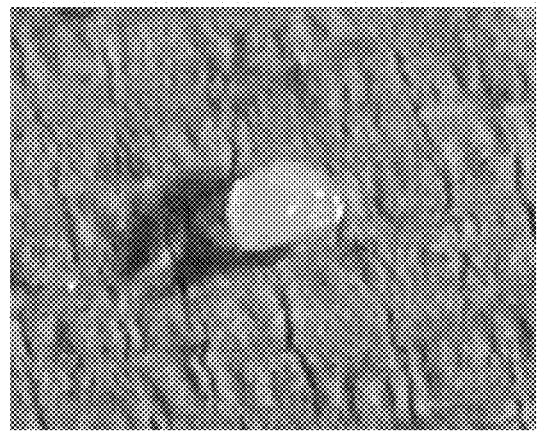
Figure 5E:
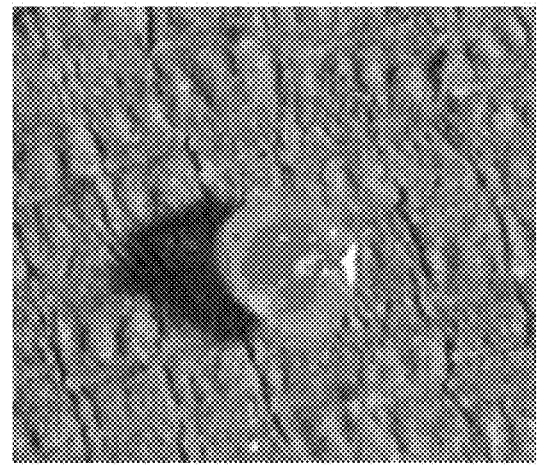
Figure 5F:
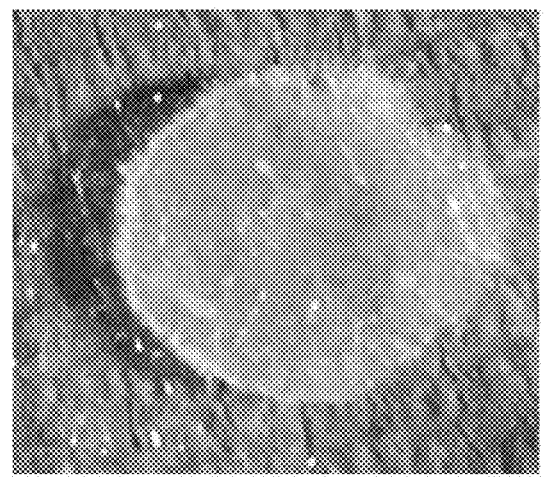

Fibers of the present invention can also be produced on an air-conditioned spinning machine (FIG. 3). The air-conditioned spinning machine is supplied with air by an ambient air-driven air conditioning unit. The air has a specific temperature and humidity. Preferably, the temperature of the air ranges from about 10° C. to about 40° C., most preferred the temperature is about 20° C. An example of such a unit is the climate testing cabinet manufactured by Weiss Umwelttechnik GmbH, model designation SB22/160/40-UKA, which was re-equipped by Weiss Umwelttechnik for recirculating air. To prevent disruptions caused by convection in the recirculating air, a tube 300 mm in diameter with 3 mm rounded holes is inserted into an insulated spinning tower 2 m in length and having an outer diameter of 680 mm. The spin tower is connected to a box within which the winding devices for the aforementioned continuous fibers or filaments are disposed. For purposes of adequate insulation, the panes of the box are made of window glass (24 mm thickness) having a K-value of 1.1. The air exiting the box is fed back to the air conditioning unit and reconditioned. The climate measuring sensor is not the interior space of the unit, but rather an external sensor disposed in the spin shaft. The air-conditioning unit is controlled (optionally also manually) by link-up to a PC supplied with the appropriate manufacturer software. Temperature and humidity programs, in addition to all other requisite unit settings, may be preset with the use of the PCC_WIN, Version 1.05 software. During the spinning operation a plotter may be used to display temperature and humidity on a time controlled basis. An additional temperature sensor has been attached for monitoring the outside temperature. This value is also recorded digitally. In the event the spinning machine is provided with process control engineering, all essential measuring points are fitted with an analog output.

The incoming and outgoing air connections between the air conditioning unit and the spin tower or box consist of flexible, double-insulated hoses with an interior diameter of 100 mm (exterior diameter: 250 mm). Each of the connectors is encased in Armaflex. Since potentially ethanol may be released from the spun composition during the spinning phase, which can accumulate within the closed loop of the air conditioner, spin tower and box, the machine has been equipped with a gas hazard warning device manufactured by GfG Gesellschaft für Gerätebau. One measurement transducer each, calibrated to ethanol, model designation MWG 0238 EX, has been mounted in the box directly adjacent the motors, and in the testing chamber of the recirculated air conditioning unit. An evaluation unit (GMA 100-BG) sounds an initial alarm if the concentration of ethanol in the chamber air reaches 25% of the lower explosive limit of the ethanol, and a second alarm if the concentration reaches 50% of the lower explosive limit. An alarm is also triggered in the event the measurement transducer experiences an outage or malfunctions.

Disposed at the upper end of the spinning tower is a slide gate valve and intermediate flange with three potential points of connection to which the double-walled, outwardly insulated spinning head is mounted. According to the test report on pressure testing the spinning head is suited to a pressure of up to 50 bar ($5 \times 10^6$ Pa). At an inner diameter of 45 mm, the spinning head holds 0.33 liters of spun composition.

An injector plate is mounted to the spinning head from below. The plate, measuring 89 mm in diameter, has an inset 1.5 mm in depth into which a stainless steel mesh encased in aluminum is inserted. The wire screen is bi-layered, the first layer having a mesh size of 80 µm.

Figure 2:
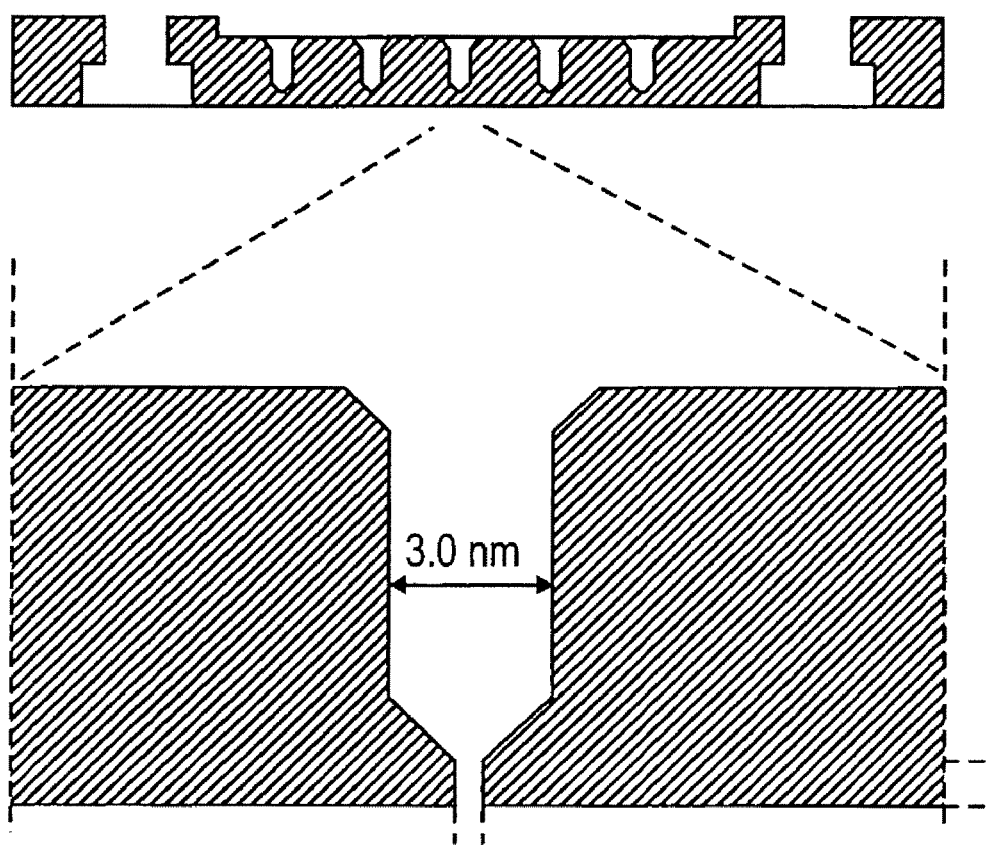
FIG. 2 shows a sketch of a hole-type nozzle in an injector plate.

A second support layer has a mesh size of 315 µm. The aluminum casing around the wire mesh is designed so that as the netting is placed in the injector plate, the former protrudes by 0.5 mm. If the plate with the mesh is screwed onto the spinning head at 15 Nm, the compressed Al-ring then supplies the requisite seal between the spinning head and plate. Seven and 19-hole injector plates were used. A hole is pre-bored to width of 3.0 mm, the hole diameter being 0.15 mm. A capillary length of 0.45 mm results in an L/D ratio of 3. A sketch of a hole-type nozzle in an injector plate is shown in FIG. 2.

The double-walled spinning head is temperature-equalized with the aid of a thermostat manufactured by LAUDA (model designation RE 112), in which the feed and exhaust hoses are insulated with Armaflex.

Inserted into the three intermediate flange connections between the spinning head and tower are viewing windows which permit observation of the threads exiting the nozzles. In designing a device for depositing filaments, consideration was also given, apart from a winding unit, to the possibility of fiber deposition by way of a gas feed nozzle. For this purpose a system for warping the filaments was constructed of 2 galettes 159 mm and 220 mm in length, respectively, in which the rear galette is angled 8° with respect to the front galette. The power drive is a motor-tacho-combination (model designation S4.3 G60) and gearing (model designation 381, 3.71:1) manufactured by Faulhaber. The rotational speed of the first galette is automatically transferred to the second galette.

Using a warp regulator the rotation of the second galette may be increased by up to 10%. A third galette serves as a winder and can be operated independently of the warp unit. The former is composed of a mandrel, also actuated by a Faulhaber motor-tacho combination, to the former of which a cardboard roller may be clamped. The cardboard roller is composed of five individual circular segments that are spring designed and bound together to form a circular diameter of 159 mm. When released, the diameter of the roller is reduced from 159 mm to 143 mm. A Teflon film is glued to the exterior of the five segments.

The third galette is mounted on a charging unit manufactured by Isel-Automation. Using a stepping motor, model designation 160 MCM, the winding apparatus is chargeable to a length of 500 mm. The charging frequency from the forward and return traverse of the unit may be adjusted to values ranging from 2 to 16 $min^{-1}$, and a second control unit can be used to move the galette manually. A control unit for the galette motors and the charging stepping motor were manufactured from Controllers (IT 142-C), a single-axle-stepping motor control with adapter card and a control card (UMS 6) from Isel-Automation. A schematic illustration of the galette-system and the air conditioning unit is shown in FIG. 3.

Hereinafter, unless stated differently, the term webbing is used synonymously for spun-bonded webbing and fibrous webbing. In a preferred embodiment of the present invention, a webbing is used to contact a wound having a periphery. The webbing is placed in or on the wound. The wound is either a primary serous secreting wound or is secondarily provided with a physiological solution, such as 0.9% sodium chloride solution, infused externally. Because the webbing is resorbed into the wound during the healing process, there is no need for its removal during healing or after the wound has healed.

The fiber density can be freely adjusted during the webbing compaction process and is variable depending upon the nature and depth of the wound. In a preferred embodiment of the present invention, a webbing is applied in or on a wound that is about 1-20 mm in depth, preferably about 2-12 mm, dependent mainly upon the thickness of the epidermis. In other embodiments, the webbing is applied to a wound larger than about 20 mm. Thus, the tissue guiding effect of the webbing is also working in larger wound extensions that is in wounds larger than about 20 mm.

Moreover, by varying the production parameters of the continuous fibers and the webbings (for example, varying the residue(s) X in $SiX_4$, reaction conditions for the hydrolytic condensation, or the ratio of non-polymerized OH-groups, and the like; see DE-C 196 09 551), it is possible to adjust the resorption rate of the fiber and consequently the resorption rate of the webbing and to adapt them to the conditions of the wound. Thus, it is feasible to adjust the resorption rate, for example, from about 3 to about 180 days depending upon requirements, with the interval being upwardly extendable as seamlessly as desired.

It is possible to control the resorption rate of the webbing and to adapt it to the moist conditions in the wound by varying the number of OH-groups in the fibers, respectively in the webbing, or by adding morphogenic factors (healing accelerators, as described further below). Morphogenic factors useful in the compositions and methods of the present invention include, but are not limited to, for example, a steroid, a cytokine, an interleukin, a bone morphogenetic protein, an antibody, TNF-α, TGF-β½, IGF, PDGF, and EGF. The morphogenic factors can be bonded to the fibers (within the webbing) either chemically via OH-groups or physically by way of physical resorption on the extremely large, highly hydrophilic surface. Thus, in a preferred embodiment of the present invention, a functional OH-group is present on every fifth to tenth Si-atom. By "functional OH-group" herein is meant an open reaction site in the form of an OH-group to which another compound can be coupled to the webbing via hydrogen bridges or condensation. In one embodiment of the present invention, the compound that is coupled to a functional OH-group of a webbing is a medication, which is then later released incrementally into the wound (drug release). A medication useful for the methods and compositions of the present invention include, but are not limited to, for example, an antibiotic, an antimycotic and other drugs having a local or systemic effect. Other useful compounds that can be coupled to the webbing in a similar way are nucleotides, amino acids and polymers thereof as described further herein. Resorption rates fluctuate at approximately 30 days.

Degradation products ($SiO_2$ and SiO(OH) as nano-particles) typically are about 0.5-1 nm in diameter. A precise structure clarification is obtained using Si-solid state NMR, in particular by measuring the Q4 mode.

In a preferred embodiment of the present invention, the pressure applied in the spinning process is from about 1 bar to about 10 bar ($10^5$-$10^6$ Pa), preferably from about 2 bar to 3 bar.

Rates of reaction in the spinning process are preferably from about 20 s to about 60 s.

Temperatures applied to the spinning process are preferably maintained at from about 15° C. to about 23° C., and particularly preferred at about 20° C.

An unexpected and surprising finding was that, most likely as a result of the fiber geometry, an acceleration in the healing of the wound (tissue guiding) is achieved. In this process the two- and three-dimensionally arranged, highly hydrophilic gel fibers function as a scaffolding to which the proliferating cells are able to adhere and to form a localized mostly collagen matrix. The chemical environment of the fibers is nearly pH neutral (pH 7.0±0.2) and no organic decomposition products are formed. Thus, no antigenic reaction or irritation in the newly generating cells is observed. Rather, the wound healing process is continuously stimulated physiologically, because of the accumulation of the aforementioned morphogenic factors some of which are also secreted from the wound to a certain extent. In contrast to organically derived gel-like and viscous matrix materials, such as collagen, hyaluronic acid, and fibrin, there is no potential risk of infection in the case of anorganic fibers with known (HIV, HBV, BSE, prions) and to date unknown sources of infection. In addition, material parameters may be very precisely defined and adjusted where anorganic materials are involved. This enhances considerably the quality and property profile of the compositions of the present invention as compared to organic materials.

In a preferred embodiment of the present invention, the webbing is manufactured in a saturated alcohol solution as described herein. Hence, the webbing is sterile. The size of a webbing may be variously selected and is adaptable to the dimensions of currently available wound dressing pads. Preferably, the size of a webbing is 10 cm×10 cm, 5 cm×5 cm or 2.5 cm×2.5 cm. Other sizes are freely selectable as well and may be chosen based on the size of the wound.

A webbing of the present invention can be suitably stored in a variety of ways. For example, the webbing is packed in a sterile and densely manner (e.g. in aluminum) and stored or dispatched for future processing. A supplemental depot, such as cotton impregnated with alcohol may also be added to the sterile packaging to maintain the saturated alcohol atmosphere.

As an alternative for storing, the webbing is directly processed to form a multilayer bandage (see, FIG. 1), that is, it can be bonded to a water impermeable (water-impervious) or semi-permeable membrane. The membrane, referred to herein also as a first membrane, may be an adhesive plaster (adhesive bandage). The membrane may also comprise a polyurethane or polyester film. In one embodiment of the present invention, the first membrane has adhesive properties and is referred to as adhesive plaster. The first membrane or adhesive plaster is indicated as 3 in FIG. 1.

During the entire preparation and production periods (from the production of the fibers to the placement of the webbing in or on the wound), the fibers and webbings are preferably maintained in a saturated alcohol-atmosphere, in order to prevent ongoing condensation of the silicon laden fibrous material and a resultant loss of biodegradability of the fibers. This is accomplished, for example, by means of a so-called in-line production process in which production proceeds within a saturated alcohol atmosphere until the final product is obtained. This provides the added advantage that once the final webbing or multilayer bandage is produced, no sterilization (for example, a gamma sterilization) is required.

1. Fiber Characteristics

A fiber of the present invention has several advantages over conventional biodegradable and/or bioresorbable biomaterials and can be distinguished from those by at least four features or characteristics. First, a fiber of the present invention allows for improved cell adhesion (adherence of cells to the fiber). Second, a fiber of the present invention facilitates cell proliferation (multiplication of cells). Third, a fiber of the present invention maintains its form and stability. Fourth, a fiber of the present invention maintains the long-term cell proliferation and cell metabolism.

a) Enhanced Cell Adhesion

The distinctive geometry and morphology of the fiber of the present invention make possible, without exception a more rapid initialization and qualitatively enhanced adhesion of cells to the surface of the fiber, as compared to conventional bioresorbable materials, such as polyglycol acid (PGA), alginates and collagens (FIG. 4). This leads to a more rapid and safer dispersion and outgrowth of cells along the fibers situated in the wound into all regions of the wound. In addition, having cells that adhere to the fibers also favors a reliable dispersion of newly formed cells distant to the fiber (cell compound proliferation). This advantageous property of the fiber of the present invention can be demonstrated by scanning-electron-microscopy (SEM), in histological and immunohistological studies and by confocal microscopy.

b) Accelerated Cell Proliferation

Unlike conventional biodegradable/bioresorbable materials, the distinctive geometry and morphology of a fiber of the present invention allows for cell proliferation that is more rapid, has an earlier onset, is accelerated and enhanced and is of longer duration or maintenance. This property furthers the advantages cited above with respect to using the fiber's characteristics to facilitate a more rapid and qualitatively enhanced adhesion of cells to the surface of the fiber.

The metabolic activity of the cells can be measured using the alamarBlue™ Assay (Biosource International, Inc., Camarillo, Calif., USA; see also, Ahmed et al., *J. Immunol. Meth.* 170:211-224 (1994); Back et al., *J. Neurosci. Methods* 91(1-2):47-54 (1999); Collins et al., *Antimicrobial Agents and Chemotherapy* 41(5):1004-1009 (1997); Desaulniers et al., *Toxicol. In Vitro* 12:409-422 (1998); Lelkes et al., *In Vitro Cell. Dev. Biol-Animal* 33:344-351 (1997); Shahan et al., *J. Immunol. Meth.* 175:181-187 (1994)). The alamarBlue™ Assay (alamarBlue™-Reduction) is briefly described. The internal environment of proliferating cells is more reduced than that of non-proliferating cells. Specifically, the ratios of NADPH/NADP, FADH/FAD, FMNH/FMN, and NADH/NAD increase during proliferation. Compounds such as alamarBlue™, which can be reduced by these metabolic intermediates, can be used to monitor cell proliferation. The oxidation-reduction potential of alamarBlue™ is +380 mV at pH 7.0, 25° C. alamarBlue™, therefore, can be reduced by NADPH (Eo=−320 mV), FADH (Eo=220 mV) FMNH (Eo=−210 mV), NADH (Eo=−320 mV), as well as the cytochromes Eo=290 mV to +80 mV). As alamarBlue™ accepts electrons from these compounds, it changes from the oxidized indigo blue, non-fluorescing state to the reduced fluorescent pink state. Proliferation can then be monitored spectrophotometrically either by color measurement or fluorescence.

Figure 6:
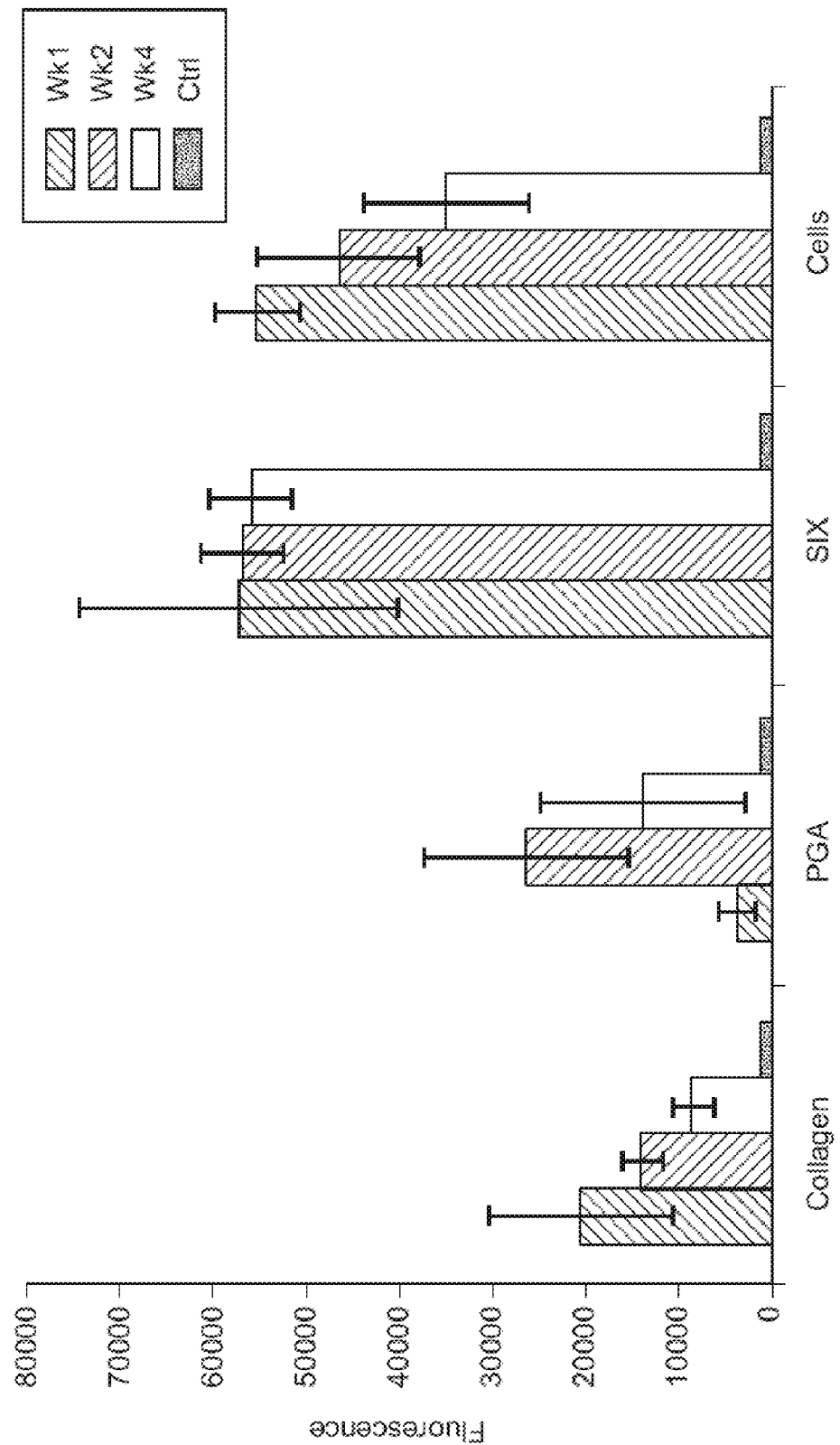
FIG. 6 shows the metabolic activity of cells (dermal fibroblasts), measured by fluorescence using the alamarBlue™ Assay, after 1, 2 and 4 weeks of cultivation with a collagen fiber (Collagen), a PGA fiber (PGA), and a $SiX_4$ fiber of the present invention (SIX) and, for purposes of comparison, without fibers (Cells).

The metabolic activity of the cells as determined by this alamarBlue™ Assay as a reference parameter for cell proliferation and cellular activity, is significantly increased after a short to mid-range period of time of 1, 2 and 4 weeks, as compared with conventional materials such as PGA and collagen (FIG. 6). The ratio of cell metabolic activity with a PGA matrix, a collagen matrix or a $SiX_4$ matrix (fiber of the present invention) is 1:5:11 (1 week), 2.5:1:6 (2 weeks) and 1.2:0.8:6 (4 weeks). Initially, (after 24 hours) the ratio was only 1:4.5:4, however. This shows that the advantages of the fiber of the present invention become apparent after a relatively lengthy time period of at least one week, more so by 4 weeks.

c) Maintenance of Fiber Shape and Stability

SEM analysis, and histological and macroscopic studies confirmed that a fiber of the present invention, unlike conventional bioresorbable materials, allows for long-term maintenance of the three-dimensional shape of the fiber and a delayed (slow) contraction of the three-dimensional fiber configuration. The fiber geometry and morphology remain largely intact. Conventional materials such as PGA and collagen shrink (sinter) over a period of 4 weeks by a factor of 4 or 6 and in some cases, also lose their shape. In contrast, a fiber of the present invention fully retains its shape and stability over the same time period. This phenomenon is illustrated in FIG. 5. This fact ensures a stable build-up of newly formed tissue and it also guarantees adequate diffusion of nutrients and metabolic products even in the case of large wounds.

In addition, unlike materials with less structural stability known in the prior art and used for this purpose such as PGA or collagen, this fact also enables and promotes the growth of new vessels. Thus, new vessel and tissue growth in large wounds and the healing thereof, is made possible for the first time using a fiber of the present invention.

In this regard, an important aspect is the shape stability of the fiber of the present invention, especially in the area of the skin, which has a mechanical stabilizing effect. Using the multilayer bandage of the present invention, the newly formed tissue is adequately supplied with nutrients. Supplying nutrients occurs not only by diffusion, but also by direct transport of the nutrients through the newly formed vessels and tissues in the open-pored webbing. With regard to shape retaining of the fiber the positive characteristics described for cell proliferation, cell adhesion are adding to this. Maintenance of fiber shape and stability was displayed using the following analytical tools: scanning-electron microscope (SEM), histology and macroscopy d) Long-Term Maintenance of Cell Proliferation and Cell Metabolism

Unlike conventional bioresorbable biomaterials, the distinctive geometry and morphology of a fiber of the present invention facilitates maintenance of cell proliferation over a long period of time thereby achieving reliable tissue build-up and regeneration. Cellular metabolic activity, determined using the alamarBlue™ Assay as a reference parameter for cell proliferation and cellular activity, is superior after a 4 week period using the $SiX_4$ fiber of the present invention, as compared to conventional biomaterials such as PGA and collagen. The ratio for collagen:PGA:$Si_4$ is 1:1.5:12 (FIG. 6).

B. Multilayer Bandages

A typical multilayer bandage in accordance with the present invention, placed in or on a wound, is shown in FIG. 1. However, other multilayer bandages are also contemplated within the scope of the present invention and these are presented below.

In a preferred embodiment of the present invention, a multilayer bandage comprises (i) a webbing (shown schematically as 1 in FIG. 1), (ii) a first membrane (shown schematically as 3 in FIG. 1), and (iii) a second membrane (shown schematically as 2 in FIG. 1).

In one embodiment of the present invention, the first membrane (3) comprises an adhesive membrane or an adhesive film. The first membrane (3) is then also referred to as an adhesive plaster or adhesive bandage. In this embodiment, the first membrane (3) or adhesive plaster represents a dressing. In another embodiment, the first membrane (3) is a simple, water impervious or semi permeable membrane or film. Adding the second membrane (2) prevents the webbing (1) from being removed from the wound (shown schematically as 4 in FIG. 1) when detaching or changing the outer-disposed first membrane (3) or adhesive plaster. The first membrane (or adhesive plaster) (3) ensures that by using the multilayer bandage of the present invention, the wound (4) is securely sealed off to the surrounding environment.

The second membrane (2) is placed on the webbing (1), that is, between the webbing (1) and the first membrane (3). According to one embodiment of the present invention, the second membrane (2) is not tightly attached with the webbing (1) nor with the first membrane or adhesive plaster (3). Still, it is possible to form a tight attachment between the second membrane (2) and the first membrane or adhesive plaster (3). Here it is essential that when removing the first membrane or adhesive plaster (3), no portion of the webbing (1) and the newly generated tissue are [ ] removed. The second membrane (2) may also be attached to the webbing (1). The attachment of the second membrane (2) to webbing (1) is achieved, for example, by means of hydrogen bridges.

The second membrane (2) may comprise a water-soluble polymer (for example, any polymer that does not bond or stick to the webbing). Preferably a water-soluble polymer of the second membrane (2) is carboxymethylcellulose (CMC). Here, the choice of polymers is not crucial (one may feasibly employ water-soluble collagens or fibrin gels), since the second membrane (2) simply ensures that the adhesive membrane or film of the first membrane or adhesive plaster (3) does not adhere to the webbing (1). This embodiment is shown in FIG. 1.

In another embodiment of the present invention, the multilayer bandage does not comprise the second membrane (2). In this embodiment, the second membrane (2) is dispensable, insofar as a dressing is used that does not adhere to the wound and functions additionally like a second membrane and/or renders the latter unnecessary. Dressings of the type that do not adhere to wounds comprise alginates (in compress form or as tamponades), collagen sponges, polyurethane foams and foam pads, hydrocolloids, hydrogels and hydropolymers. In this case, the first membrane (or adhesive plaster) (3), in order to seal off the wound as shown in FIG. 1, is fastened by means of an adhesive (on the undamaged skin tissue surrounding the wound). Preferred adhesives for the methods and compositions of the present invention include, but are not limited to, for example, poly-acylate adhesive, (India) rubber adhesive, and synthetic (India) rubber adhesives manufactured by a hot-melt method as known in the art.

In yet another embodiment of the present invention, the multilayer bandage comprises a dressing. A dressing used in the methods and compositions of the present invention seals off the wound to the surrounding environment. The dressing can be applied to the webbing (1), for example, on top of the webbing (1). Preferably, the dressing does not adhere to the wound (4) (and thus again functions like a second membrane (2) and/or renders the latter unnecessary), but still has adhesive properties and thereby seals the wound (4) off from the outside. In a preferred embodiment of the present invention, the dressing is a foam bandage, in particular a polyurethane foam bandage, because such foam bandages have a high fluid storage capacity (Bello and Phillips, *JAMA* 283(6):716-718

(2000); Degreef, *Dermatol Clin* 16(2):365-375 (1998); Findlay, *Am Fam Physician* 54(5):1519-1528 (1996); Habif, Clinical Derm, Moshby, pp. 810-813 (1996); Knapp, Ped Clin N Am 46(6):1201-1213 (1999); Krasner, Prevention Management Pressure Ulcers, (1995); Lewis, Med-Surg Nursing, Moshby, pp 199-200; Lueckenotte, Gerontologic Nurs, Moshby, pp. 800-807 (1996); PUGP, *Am Fam Physician*, 51(5):1207-1222 (1995); PUGP, Pressure Ulcer Treatment, AHCPR 95-0653 (1994); Way, Current Surgical, Lange, pp. 95-108 (1991)). Foam bandages particularly useful for the methods and compositions of the present invention include, but are not limited to, for example, foam dressing from 3M, Silastic from Dow Corning (distributed by Calmic Medical Division), Allevyn from Smith and Nephew, und Lyofoam from Seton Healthcare Group plc.

According to still another embodiment of the present invention, it is possible to omit completely (without substitution) the second membrane (2) when the first membrane (3) (in this case not necessarily adhesive) is applied directly to the webbing (1). In this embodiment, the adhesive membrane or film of the first membrane (or adhesive plaster) (3) forms an adhesive bond exclusively with the skin tissue on the perimeter of the wound (4), thereby making it impossible for the first membrane (3) to bond with the webbing (1). This is achieved, for example, by applying to the skin tissue on the wound periphery an adhesive, for example, Leukospray™ (Baiersdorf), prior to the occlusion process. In such case, the first membrane (3) is itself non-adhesive and is thus more accurately characterized as a first membrane (3), rather than adhesive plaster or adhesive bandage. Alternatively, this can be achieved by selecting or cutting to size the first membrane or adhesive plaster (3) to correspond to the size of the wound (4). In this case, the adhesive plaster is adhesive only at those points not directly contacting the wound (4).

According to the present invention the first membrane (3) is composed of a water-impervious film made of at least one water-insoluble polymer. The water-insoluble polymer, for example, can be polypropylene (PP), polyvinylchloride (PVC) or polyurethane (PU). In another embodiment of the present invention, the first membrane (3) further comprises an adhesive conventionally used in bandage technology, which preferably exhibits particularly strong skin tissue compatibility. Adhesives particularly useful for the methods and compositions of the present invention include, but are not limited to, for example, polyacrylate adhesives and synthetic (India) rubber adhesives. These are hypoallergenic and have strong tissue compatibility. The adhesive can be applied to the water-impervious film immediately upon or prior to assembly of the multilayer bandage. However, it can also be applied or sprayed by the user, as described above, to an area on the perimeter of the wound, or to the membrane or film.

A water-impervious adhesive plaster (3) or water-impervious first membrane (3) ensures that no moisture can evaporate outwardly, thereby maintaining permanently a moist wound environment which aids in the resorption of the webbing fibers. Resorption of the fibers also causes substances potentially bound to the fibers to be released, that is, a release and accumulation of ions (for example, Ag-ions), medications (for example, an antibiotic, an antimycotic, or a corticoid) or morphogenic factors. Morphogenic factors (also referred to as morphogenes), to be used in the methods and compositions of the present invention include, but are not limited to, for example, a steroid, a cytokine, an interleukin, a bone morphogenetic protein (BMP), an antibody, TGF-β, IGF, TNF-α, PDGF, and EGF. Morphogenic factors are also formed to a certain extent by the organism during wound healing. Generally, morphogenic factors exert a favorable influence on, and are indispensable for proper wound healing.

The water solubility of the polymer of the second membrane (2) makes it easy to loosen the membrane (when present) after a certain period of exposure. This is possible because the hydrous wound exudates gradually loosens the webbing (1) from the second membrane (2) so as not to result in damage to the tissue as the second membrane (2) is lifted off. To reduce the risk of infection, polymers doped with silver are advantageously employed as a second membrane (2).

In the case of particularly large wounds (>10 cm$^2$) a floating bandage is expedient, because under certain circumstance the adhesive forces of a second membrane (2) to the webbing (1) would become too great. In such cases it is possible to use a separation medium in the form of hydrogels as a thin (<5 mm) floating layer.

If needed additional bandage material (for example, bandage gauze) or other materials, such as for padding or protection may be applied to the multilayer bandage as described in its various embodiments according to the present invention. Thus, within the scope of the present disclosure a distinction is made between dressing and bandage material. In one embodiment of the present invention, dressing is a component of the multilayer bandage. Bandage material is basically used as a pad for protection of the wound. There is no direct contact between bandage material and webbing, i.e., between bandage material and the bioresorbable fibers.

Prior to placing the webbing (1) in or on a wound (4) or further processing it to form a multilayer bandage (i.e. after manufacture, in storage or during transport, be it as webbing (1) only or forming a multilayer bandage), it is preferable to insulate with a thick membrane the surface of the webbing that is subsequently in contact with the wound. This membrane serves to prevent leakage of the alcohol. This membrane can easily be removed by the user, optionally directly prior to application on the wound. It is important to note that alcohol, as discussed above, stabilizes the sterility and chemistry of the fibers, but it is extremely painful when brought in contact with the wound. Therefore, in accordance with another preferred embodiment of the present invention, physiological saline may be used as a medium. Alternatively, it is possible to evaporate or rinse out the alcohol prior to use.

Typical dressings to which the webbing may be fitted include, but are not limited to the following products (by trademark): Dermaplast Film/Active™ and Hydractive™; Hydrofilm PlusTM™; Hydrocoll™ (Hartmann); Comfeel (-Plus)™, Biatain™, Seasorb™, Contreet™ (Coloplast), Cutinova Hydro™, Acticoat™, and Allevyn™ (Smith & Nephew).

The webbing (1) may also be combined with products currently on the market in all their variations, for example with the following Smith & Nephew products: Hydrogel-bandages™, IntraSite ConformableTM®, IntraSite GelTM™, hydro-selective wound dressings, Cutinova Hydro™ (for example, hydro cellular foam wound dressings), Allevyn™ product group (for example, alginate, antimicrobial wound dressings, enzymatic debridement, odor-resorbing bandages, post-operative-bandages), Cutiplast Steril™, Hansapor Steril™, OpSite Post-OpTM®, Primapore™ (for example, specialty bandages), Allevyn Tracheostomy™, Cavi-Care™, and EXU-DRY™.

Thus, the webbing (1) may be combined, for example, with polyurethane or PVA-sponge dressings to enhance resorbence in the case of heavily exudating wounds. The aforementioned advantages of the present invention are particularly evident in the use of vacuum systems (for example, V.A.C™), for example in the treatment of septic wounds and where antibiotic flushing is required. In addition, the webbing may be combined with the alginate-tamponade described above as a covering for use in hydrocolloid wound dressings.

The shape of the multilayer-bandage may vary depending on the location of the wound, as well as its shape and size, to thereby obtain a maximally precise fit with the anatomy of the wound. One optional bandage shape is the butterfly bandage for application in the anal region.

In one embodiment of the present invention, the aforementioned multilayer bandage has the following structure: (i) a webbing (1) for placement in direct contact with a wound (4), and (ii) a first membrane (3) which is water impervious and comprises at least one water insoluble polymer, wherein the first membrane (3) is an adhesive plaster and comprises an adhesive portion that bonds with skin tissue at a wound periphery.

In another embodiment the first membrane (3) does not comprises an adhesive portion and bonds with an adhesive which is applied to the skin tissue at said wound periphery, and wherein a loose, frangible adhesive bond or no adhesive bond at all exists between the first membrane (3) and the webbing (1). The term "loose, frangible adhesive bond" means an adhesive bond that is capable of being broken easily but does not necessarily imply an inherent weakness.

A preferred multilayer bandage of the present invention is one wherein the first membrane (3) is as described herein and wherein the webbing (1) comprises a biologically degradable and/or resorbable fiber structure. This fiber structure is obtained, for example, by drawing fibers from a spun composition. A spun composition, as described herein, comprises one or more partially or completely hydrolytically condensed silicon compounds that are obtained by hydrolytic condensation of monomers of the general formula $SiX_4$. $SiX_4$ is a tetravalent compound comprising residues $X_1$, $X_2$, $X_3$, and $X_4$. In one embodiment of the present invention, residues $X_1$, $X_2$, $X_3$, and $X_4$ are identical. In another embodiment of the present invention, residues $X_1$, $X_2$, $X_3$, and $X_4$ are different. In a preferred embodiment of the present invention, residues $X_1$, $X_2$, $X_3$, and $X_4$ are independently selected from the group consisting of hydroxyl, hydrogen, halogen, amino, alkoxy, alkyloxy, alkylcarbonyl and alkoxycarbonyl. As used herein, the term "halogen" refers to the elements including fluorine (F), chlorine (Cl), bromine (Br) and iodine (I). The term "alkoxy" refers to alkyl radicals attached to the remainder of a molecule by an oxygen, e.g., ethoxy, methoxy, or n-propoxy. The term "alkoxy" also refers to a heteroalkyl that contains one or more oxygen heteroatoms.

In yet another embodiment two residues, for example $X_1$ and $X_2$ are identical and two residues, for example $X_3$ and $X_4$ are different. In another embodiment, three residues, for example $X_1$, $X_2$, and $X_3$ are identical and one residue, for example $X_4$ is different.

In another embodiment, residues $X_1$, $X_2$, $X_3$, and $X_4$ are derived from an alkyl and can be interrupted by one or more oxygen atoms, sulfur atoms or amino groups. As used herein, the term "alkyl" refers to a straight or branched chain hydrocarbon radical, and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

A preferred multilayer bandage of the present invention is a multilayer bandage wherein residues $X_1$, $X_2$, $X_3$, and $X_4$ of $SiX_4$ are identical and are ethyl.

1. Multilayer Bandages Wherein The Hydrolytic Condensation Occurs in the Presence of Organic Compounds Hydrolytic condensation as described herein can be performed in the presence of several organic compounds, preferably nucleotides or amino acids and polymers thereof. The presence of the amino acid(s), and/or peptide(s) and/or DNA molecules or DNA fragments leads to their incorporation into the fibers. In one embodiment of the present invention, incorporation of these organic compounds is through covalent bonds. In another embodiment, incorporation is by non-covalent bonds.

Once the multilayer bandage is applied to the wound the amino acid(s), peptide(s), DNA molecule(s) or DNA fragments are released from the bandage at a rate which corresponds to the rate of degradation of the fibers. The amount of amino acid(s), peptide(s), DNA molecule(s) or DNA fragments released is determined by the amount of amino acid(s), peptide(s), DNA molecule(s) or DNA fragments incorporated into the fibers while the rate of release from the fibers is determined by the rate of degradation of the fibers.

Cell adhesion, an attribute of the fiber as described above, enables to a significant extent the take up of the amino acid(s), peptide(s), DNA molecule(s) and/or DNA fragment(s) into the proliferating cells. In particular this take-up ensures that the cells can be directly influenced by the peptide(s) or by the genetic information encoded by the nucleic acid. This is especially important and of use where wounds with reduced regional or even systemic metabolic rates are concerned, because it ensures, for example, an external supply to the wound region of amino acids necessary in cell metabolic activity, making wound healing feasible.

a) Multilayer Bandages wherein the Hydrolytic Condensation Occurs in the Presence of One or More Amino Acids or Peptides In a preferred embodiment of the present invention, the multilayer bandage is a multilayer bandage wherein the hydrolytic condensation occurs in the presence of one or more amino acids. In one preferred embodiment of this multilayer bandage, the residues X in the formula $SiX_4$ are identical and are ethyl.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to a compound that has the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetic" refers to a chemical compound that has a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Another preferred multilayer bandage of the present invention is a multilayer bandage wherein the hydrolytic condensation occurs in the presence of one or more peptides. In one preferred embodiment of this multilayer bandage, the residues X in the formula $SiX_4$ are identical and are ethyl.

The terms "peptide," "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor & Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by independent tertiary units, usually by noncovalent association.

In a preferred embodiment of the present invention, the hydrolytic condensation occurs in the presence of morphogenic factors described above.

b) Multilayer Bandages wherein the Hydrolytic Condensation Occurs in the Presence of One or More Nucleotides, Nucleic Acids, Oligonucleotides, or Polynucleotides Another preferred multilayer bandage of the present invention is a multilayer bandage wherein the hydrolytic condensation occurs in the presence of one or more nucleotides, nucleic acids, oligonucleotides, polynucleotides, DNA molecules or DNA fragments. In one preferred embodiment of this multilayer bandage, the residues X in the formula $SiX_4$ are identical and are ethyl.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000 nucleotides, etc. A nucleic acid will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see, Eckstein, *Oligonucleotides and Analogues: A Practical Approach*, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O methylphosphoroamidite linkages (see, Eckstein, *Oligonucleotides and Analogues: A Practical Approach*, Oxford University Press), and peptide nucleic acid backbones and linkages (see, Egholm, *J. Am. Chem. Soc.* 114:1895 (1992); Meier et al., *Chem. Int. Ed. Engl.* 31:1008 (1992); Nielsen, *Nature* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "*Carbohydrate Modifications in Antisense Research*", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non ribose backbones, including those described in U.S. Pat. Nos. 5,235,033 and 5,034,506, and Chapters 6 and 7, ASC Symposium Series 580, "*Carbohydrate Modifications in Antisense Research*", Ed. Y. S. Sanghui and P. Dan Cook. Nucleic acids containing one or more carbocyclic sugars are also included within one definition of nucleic acids (see, Jenkins et al., *Chem. Soc. Rev.* pp 169 176 (1995)). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. Typically, PNAs are not degraded by cellular enzymes, and thus can be more stable.

The nucleic acids may be single stranded or double stranded, or contain portions of both double stranded or single stranded sequences. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. RNA typically refers to a naturally occurring RNA, e.g., a pre-mRNA, hnRNA, or mRNA. The nucleic acid may be a naturally occurring nucleic acid or may be synthesized de novo either chemically or by using recombinant DNA methodology.

In a preferred embodiment of the present invention, the hydrolytic condensation occurs in the presence of a nucleic acid encoding a morphogenic factor described above.

C. Kits

The invention also provides kits that can be used for accelerated wound healing as described herein. In a preferred embodiment of the present invention, a kit comprises a multilayer bandage embracing the specifics as outlined herein, wherein the multilayer bandage is used for accelerated wound healing. The kit may further comprise instructions for using the compositions of the present invention in accelerating wound healing.

Further, kits are provided comprising compositions described herein that allow the user to practice the methods of the invention. As indicated above, the kits may include instructional materials containing directions (e.g., protocols) for the practice of this invention. While the instructional materials typically comprise written or printed materials they are not limited to such. Any medium capable of storing such instructions and communicating them to an user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

All publications, patents and patent applications cited in this specification are herein incorporated in their entireties by reference as if each individual publication, patent or patent application were specifically and individually indicated to be incorporated by reference.

What is claimed is:

1. A method for the accelerated healing of a wound, the method comprising:
    applying a multilayer bandage to the wound, wherein the multilayer bandage comprises (i) a spun-bonded webbing comprising at least one partially or completely hydrolytically condensed silicon compound and (ii) a water-impervious or semi-permeable first membrane comprising at least one water-insoluble polymer, wherein the webbing has a biologically degradable or biologically resorbable structure, wherein the webbing is brought into direct contact with said wound by placing the webbing in or on the wound and further wherein the first membrane seals the wound off from the surrounding environment when the multilayer bandage is applied to the wound.

2. The method of claim 1, wherein the water-insoluble polymer of the first membrane is selected from the group consisting of polypropylene, polyvinylchloride and polyurethane.

3. The method of claim 1, wherein the first membrane is a self-adhesive hydropolymer.

4. The method of claim 1, wherein the webbing is a fibrous webbing.

5. The method of claim 1, wherein the silicon compound comprises a monomer of the formula $SiX_4$ wherein residues $X_1, X_2, X_3$, and $X_4$ are independently selected from the group consisting of hydroxyl, hydrogen, halogen, amino, alkoxy, alkyloxy, alkylcarbonyl and alkoxycarbonyl.

6. The method of claim 1, wherein the silicon compound comprises a monomer of the formula $SiX_4$ wherein residues $X_1, X_2, X_3$, and $X_4$ are alkyl residues and are optionally interrupted by an oxygen atom, a sulfur atom or an amino group and wherein said residues $X_1, X_2, X_3$, and $X_4$ are identical or different.

7. The method of claim 6, wherein the residues $X_1, X_2, X_3$, and $X_4$ are ethyl.

8. The method of claim 7, wherein the webbing comprises a morphogenic factor selected from the group consisting of a steroid, a cytokine, an interleukin, a bone morphogenetic protein, an antibody, TNF-α, TGF-β½, IGF, PDGF, and EGF.

9. The method of claim 1, wherein the webbing comprises an organic compound selected from the group consisting of a nucleotide, an amino acid and polymers thereof.

10. The method of claim 1, wherein the wound healing multilayer bandage further comprises (iii) a second membrane comprising at least one water-soluble polymer, the second membrane being disposed between the first membrane and the webbing.

11. The method of claim 10, wherein the water-soluble polymer is carboxymethylcellulose.

12. The method of claim 10, wherein the second membrane is bonded to the webbing by a loose, frangible adhesive bond.

13. The method of claim 10, wherein the second membrane is not adhesively bonded to the webbing.

14. The method of claim 10, wherein the first membrane is bonded to the second membrane by a loose, frangible adhesive bond or a stable, non-frangible adhesive bond.

15. The method of claim 10, wherein the dressing is bonded to the first membrane by either a loose, frangible adhesive bond or a stable, non-frangible adhesive bond.

16. The method of claim 1, wherein the wound has a wound periphery, wherein the first membrane is water-impervious and (a) further comprises an adhesive portion which adheres to skin tissue at the wound periphery or (b) does not comprise an adhesive portion and bonds with an adhesive which is applied to the skin tissue at the wound periphery; and
    either the first membrane is not bonded to the webbing or is bonded to the webbing by a loose, frangible adhesive bond, and the multilayer bandage further comprises (iii) a dressing selected from the group consisting of an alginate, a collagen sponge, a polyurethane foam, a polyurethane foam pad, a hydrocolloid, a hydrogel and a hydropolymer, disposed between the webbing and the first membrane.

17. The method of claim 16, wherein the dressing is bonded to the webbing by a loose, frangible adhesive bond.

18. The method of claim 16, wherein the dressing is not bonded to the webbing.

19. A method for the accelerated healing of a wound, the method comprising:

applying a multilayer bandage to the wound, wherein the multilayer bandage comprises (i) a spun-bonded webbing comprising at least one partially or completely hydrolytically condensed silicon compound and (ii) a water-impervious or semi-permeable first membrane comprising at least one water-insoluble polymer, wherein the webbing has a biologically degradable or biologically resorbable structure, wherein the webbing is brought into direct contact with the wound by placing the webbing in or on the wound and further wherein a moist wound environment for the wound is maintained when the multilayer bandage is applied to the wound.

20. The method according to claim 19, wherein the first membrane prevents moisture from evaporating outwardly from the wound through the first membrane when the multilayer bandage is applied to the wound.

* * * * *